US00PP17133P2

(12) United States Plant Patent
Egger

(10) Patent No.: US PP17,133 P2
(45) Date of Patent: Oct. 3, 2006

(54) ***HEUCHERA* PLANT NAMED 'TANGO'**

(50) Latin Name: ***Heuchera* hybrid**
Varietal Denomination: Tango

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 3 days.

(21) Appl. No.: 11/158,496

(22) Filed: Jun. 21, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Klarquist Sparkman, LLP

(57) ABSTRACT

A new and distinct hybrid of *Heuchera* plant characterized by veiled, chocolate colored foliage, hot pink flowers on short dark stalks, a mounding habit, and excellent vigor.

1 Drawing Sheet

Botanical denomination: *Heuchera* hybrid.
Variety designation: 'Tango'.

The present invention relates to a new and distinct cultivar of *Heuchera* hybrid and given the cultivar name of 'Tango'. *Heuchera* is in the family Saxifragaceae. *Heuchera* 'Tango' originated from a cross between *Heuchera* 44-1 (an unpatented, experimental, proprietary plant) as the seed parent, and *Heuchera* 133-3 (an unpatented, experimental, proprietary plant) as the pollen parent. Given its ornamental foliage and flower form, it is probable that *Heuchera. sanguinea, H. americana,* and *H. micrantha* are in its parentage.

This new *Heuchera* is distinguished by:

1. Chocolate brown, silver-veiled foliage
2. Hot pink flowers on numerous, dark flowering stems
3. Mounding habit
4. Excellent vigor This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a two-year-old plant of *Heuchera* 'Tango' growing in a two gallon container in the shade house in May in Canby, Oreg.

FIG. 2 shows a close up of the leaves and flowers.

DETAILED PLANT DESCRIPTION

The following is a detailed description of the new *Heuchera* cultivar based on observations taken in May of a two-year-old specimen grown a two gallon container in an open air shade house with 50% shade cover and added irrigation in the summer months in Canby, Oreg. Canby is in Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Botanical denomination: *Heuchera* hybrid.
Variety designation: 'Tango'.
Parentage: *Heuchera* 44-1×133-3 (both proprietary, unreleased plants).

Plant:
- *Form.*—Basal rosette, herbaceous perennial.
- *Hardiness.*—USDA Zone 4 to 9.
- *Size.*—14 cm tall from the top of the soil to the top of the foliage and 43 cm wide.
- *Habit.*—Mounding.
- *Vigor.*—Excellent.
- *Roots.*—Fibrous, freely branching, fine, and white in color. Roots develop easily from cuttings.

Leaf:
- *Type.*—Simple.
- *Arrangement.*—Rosette.
- *Shape.*—Ovate to orbicular.
- *Lobing/division.*—7 shallow lobes.
- *Venation.*—Palmate.
- *Margins.*—Crenate, undulate.
- *Apex.*—Mucronulate.
- *Base.*—Cordate, lobes strongly overlapping at the base.
- *Blade size.*—5 to 7 cm long and 5 to 7.5 cm wide.
- *Surface texture.*—Glandular hairs on both sides.
- *Petiole.*—7.5 to 14 cm long and grows to 3 mm wide.
- *Petiole surface.*—Glandular.
- *Petiole color.*—Greyed Purple 187A.
- *Leaf color.*—Topside — From spring Greyed Purple 187A with a veil of Greyed Purple 186D to Brown 200A with a veil of Greyed Green 198D to winter Brown 200B with little or no veil of Greyed Green 198D. Bottom side — Red Purple 59A with more purple tones on younger leaves.

Inflorescence:
- *Type.*—Thyrse.
- *Number of flowers.*—70 per thyrse.

*Number of thyrse in spring.*—31.

*Peduncle.*—29 to 48 cm tall and 2.5 mm wide near base, with no cauline leaves, Greyed Purple 187A, surface with glandular hairs.

*Pedicel.*—Variable in size, Grayed Purple 187A, with glandular hairs.

*Bloom period.*—May in Canby, Oreg.

Flower bud:

*Size.*—3 mm wide and 7 mm long.

*Description.*—Glandular, ovoid.

*Color.*—Red Purple 63A.

Flower:

*Type.*—Perfect, zygomorphic.

*Shape.*—Campanulate.

*Size.*—8.5 mm long and 6 mm wide.

*Petal description.*—5 in number, inconspicuous, 3 mm long and 1 mm wide, spatulate with a clawed base, apex acute, margins entire, Red Purple 63C on both sides, backs sparsely glandular.

*Calyx description.*—8.5 mm long and 6 mm wide, with 5 lobes, divided ⅓ way to the base, glandular on both sides, apex acute, margins entire, Red Purple 63A at both ends and Red Purple 63AB in the middle on both sides.

*Stamen description.*—5 in number, filaments 3 mm long and light pink, Red Purple 63C, anthers sterile, no pollen produced, Yellow Green 153B.

*Pistil description.*—White 155B overall, 8 mm long.

*Fragrance.*—None.

*Lastingness.*—Each thyrse blooms for about 2 weeks on the plant.

Fruit:

*Type.*—Two-beaked ovoid capsule.

*Color.*—Brown 200D.

Seed:

*Shape.*—Linear.

*Size.*—2 mm long.

*Color.*—Black 202A.

Pest and disease tolerance: Excellent disease resistance to powdery mildew, the common problem of *Heuchera*. Susceptible to *Heuchera* rust and root weevils.

COMPARISON TO SIMILAR *HEUCHERA*

Compared to *Heuchera* 'Vesuvius' (U.S. Plant Pat. No. 13,215), this new variety has darker leaves with undulating margins, shorter flower stalks, and hot pink rather than dull red flowers.

Compared to *Heuchera* 'Cherries Jubilee' (U.S. Plant Pat. No. 11,377), *Heuchera* 'Tango' has darker leaves with undulating margins and hot pink flowers rather than dull red flowers.

Compared to *Heuchera* 'Hollywood' (U.S. Plant patent application Ser. No. 11/155,215), the new variety has hot pink rather than coral flowers. H. 'Hollywood' has wand type flowers while the new variety does not. Both are compact growing plants with dark, veiled leaves and short flowering stems.

Compared to the seed parent, *Heuchera* 44-1, the new variety has much larger, brighter pink flowers on shorter flowering stems and darker leaves.

Compared to the pollen parent, *Heuchera* 133-3, the new variety has larger, hot pink rather than medium pink flowers and shorter flowering stems. Both are very free flowering.

I claim:

1. A new and distinct hybrid of *Heuchera* plant as herein illustrated and described.

* * * * *

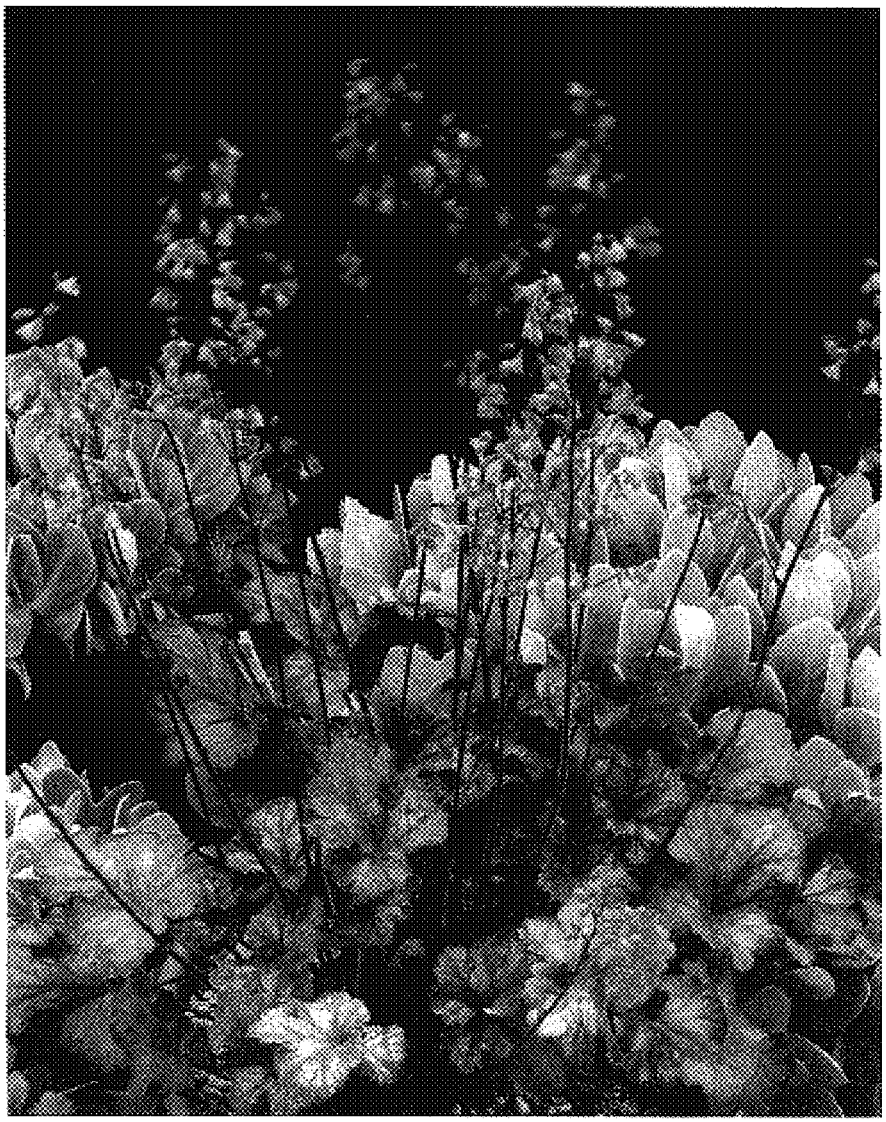
Figure 1 above
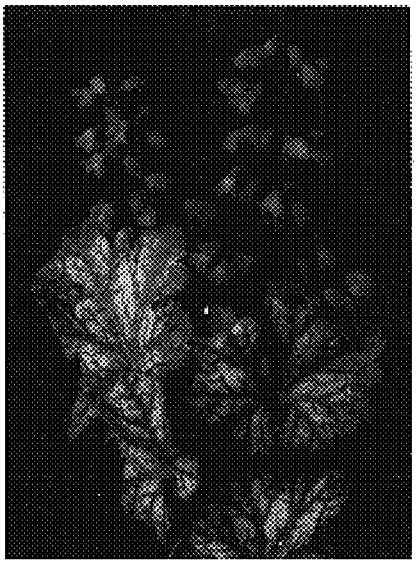
Figure 2